United States Patent
Gencer et al.

(10) Patent No.: US 10,123,704 B2
(45) Date of Patent: Nov. 13, 2018

(54) METHOD AND SYSTEM FOR DUAL-BAND ACTIVE THERMAL IMAGING USING MULTI-FREQUENCY CURRENTS

(71) Applicants: Nevzat Guneri Gencer, Ankara (TR); Hamza Feza Carlak, Ankara (TR); Cengiz Besikci, Ankara (TR)

(72) Inventors: Nevzat Guneri Gencer, Ankara (TR); Hamza Feza Carlak, Ankara (TR); Cengiz Besikci, Ankara (TR)

( * ) Notice: Subject to any disclaimer, the term of this patent is extended or adjusted under 35 U.S.C. 154(b) by 556 days.

(21) Appl. No.: 14/903,057

(22) PCT Filed: Jul. 5, 2013

(86) PCT No.: PCT/TR2013/000206
§ 371 (c)(1),
(2) Date: Jan. 5, 2016

(87) PCT Pub. No.: WO2015/002618
PCT Pub. Date: Jan. 8, 2015

(65) Prior Publication Data
US 2016/0135686 A1 May 19, 2016

(51) Int. Cl.
*A61B 5/00* (2006.01)
*A61B 5/01* (2006.01)
(Continued)

(52) U.S. Cl.
CPC .......... *A61B 5/0035* (2013.01); *A61B 5/0093* (2013.01); *A61B 5/015* (2013.01);
(Continued)

(58) Field of Classification Search
CPC ... A61B 5/0035; A61B 5/0093; A61B 5/6823; A61B 5/053; A61B 5/4312; A61B 5/05;
(Continued)

(56) References Cited

U.S. PATENT DOCUMENTS 7,214,195 B2 * 5/2007 Mitra .................... A61B 5/015
600/473
7,485,882 B2 2/2009 Zombo et al.
(Continued)

FOREIGN PATENT DOCUMENTS

GB 2294604 A 5/1996
WO WO2011/080712 A1 7/2011

OTHER PUBLICATIONS

P. T. Huynb, A. M. Jarolimek, S. Daye 1998, "The False-negative Mammogram," Radiographics, 18(5), pp. 1137-1154.
(Continued)

*Primary Examiner* — Sanjay Cattungal
(74) *Attorney, Agent, or Firm* — Gokalp Bayramoglu (57) ABSTRACT

A hybrid system is developed using thermal and electrical impedance imaging methods together. The innovation of the approach relies on the frequency dependence of the tissue's electrical impedance which facilitates the acquisition of multiple thermal images with currents at different frequencies injected to the region of the body under inspection. Proposed method without current application (in passive mode of operation) provides images which are obtained by standard thermal imagers. On the other hand, the application of the electrical current (in active mode of operation) increases the temperature contrast on the body surface depending on the electrical property of tissue. Therefore, the technique while increasing the thermal contrast provides frequency dependent conductivity distribution data which can be used as a basis for the detection of the breast carcinoma. The sensitivity of the technique is increased by an infrared camera with dual band (MWIR/LWIR) imaging capability.

9 Claims, 4 Drawing Sheets (51) Int. Cl.
A61B 5/05 (2006.01)
G06T 7/00 (2017.01)
A61B 5/053 (2006.01)

(52) U.S. Cl.
CPC ............... *A61B 5/05* (2013.01); *A61B 5/053* (2013.01); *A61B 5/4312* (2013.01); *A61B 5/6823* (2013.01); *G06T 7/0012* (2013.01); G06T 2207/10048 (2013.01); G06T 2207/30068 (2013.01)

(58) Field of Classification Search
CPC .................. A61B 5/015; G06T 7/0012; G06T 2207/30068; G06T 2207/10048
USPC .................................................. 600/473–480
See application file for complete search history.

(56) References Cited

U.S. PATENT DOCUMENTS

| | | | |
|---|---|---|---|
| 8,812,084 B1* | 8/2014 | Messano, Jr. ............ | A61B 5/05 600/473 |
| 2004/0217289 A1 | 11/2004 | Raulerson et al. | |
| 2004/0236225 A1 | 11/2004 | Murphy et al. | |
| 2005/0020924 A1* | 1/2005 | Mitra ..................... | A61B 5/015 600/474 |
| 2007/0156062 A1* | 7/2007 | Mitra ..................... | A61B 5/015 600/549 |
| 2007/0161922 A1 | 7/2007 | Dekel et al. | |
| 2007/0213617 A1 | 9/2007 | Berman et al. | |
| 2008/0260225 A1 | 10/2008 | Szu | |

OTHER PUBLICATIONS

H.Qi, N.A. Diakides,2003, "Thermal Infrared Imaging in Early Breast Cancer Detection—A Survey of Recent Research," IEEE Embs 25th Annual International Conference,pp. 1109-1112.

J.C. Newell, 2002, "Special issue on electrical impedance imaging," IEEE Transactions on Medical Imaging, 21, pp. 6.

S. U. Eker, M. Kaldirim, Y. Arslan, and C. Besikci, 2008, "Large-Format Voltage-Tunable Dual-Band Quantum Well Infrared Photodetector Focal Plane Array for Third-Generation Thermal Imagers," IEEE Electron Device Letters, 29 (10), pp. 1121-1123.

N. A. Diakides, J. D. Bronzino, 2006, "Medical Infrared Imaging," CRC Press, pp. 9.1-9.18.

C. Gros, M. Gautherie, 1980, "Thermography and Cancer Risk Prediction," Cancer, pp. 45-51.

A. W. Guy, 1971, "Analyses of Electromagnetic Fields Induced in Biological Tissues by Thermographic Studies on Equivalent Phantom Models," IEEE Transactions on Microwave Theory and Techniques, 19-2, pp. 205-214.

M. Mital, E. P. Scott, 2007, "Thermal Detection of Embedded Tumors Using Infrared Imaging," Journal of Biomechanical Engineering, 129, pp. 33-39.

F. J. Gonzalez, 2007, "Thermal Simulation of Breast Tumors," Instituto de Investigacion en Comunicacion Optica, Universidad Autonoma de San Luis Potosi, 53, pp. 323-326.

L. Jiang, W. Zhan, M. H. Loew 2011, "Modeling Static and Dynamic Thermography of the Human Breast under Elastic Deformation," Phys. Med. Biol., 56, 187-202.

B. F. Jones, 1998, "A Reappraisal of the Use of Infrared Thermal Image Analysis in Medicine," IEEE Transactions on Medical Imaging, 17, pp. 1019-1027.

N. M. Sudharsan, E. Y. K. Ng, 2000, "Parametric Optimization for Tumor Identification: Bioheat Equation Using ANOVA and the Taguchi Method," Journal of Engineering in Medicine, 214, pp. 505-512.

http://www.breastthermography.com/infrared_imaging_review.htm, last visited: Dec. 24, 2015.

J. R. Keyserlingk, P.D. Ahlgren, E. Yu, N. Belliveau, M. Yassa, "Functional Infrared Imaging of the Breast," IEEE Engineering in Medicine and Biology Magazine, 19, pp. 30-41.

Y. Ohashi, I. Uchida, 2000, "Applying Dynamic Thermography in the Diagnosis of Breast Cancer," IEEE Engineering in Medicine and Biology Magazine, 19, pp. 42-51.

M. Kaczmarek, A. Nowakowski, 2004, "Active Dynamic Thermography in Mammography," Task Quarterly, 8(2), pp. 259-267.

P. M. Arabi, 2008, "Breast Carcinoma Detection at early Stage by FIR radiation of Microwave heated Breast Tissues," Proceedings of the 2008 International Conference on Computing, Communication and Networking.

L. TH Thomassin, D. Giraud, 1984, "Detection of Subclinical Breast Cancers by Infrared Thermography," Proceedings of the Third International Congress of Thermology pp. 575-579.

R. Joro, A. L. Laaperi, P. Dastidar, S. Soimakallio, 2008, "T. Kuukasjarvi, Imaging of breast cancer with mid- and long-wave infrared camera," Journal of Medical Engineering & Technology, 32, pp. 189-197.

H. F. Carlak, N. G. Gencer, 2009, "Elektriksel Olarak Uyarilmi ş Göğüs Modelinin Termal Görüntüleme Simülasyonlari," 14. Biyomedikal Mühendisliği Ulusal Toplantisi.

H. F. Carlak, N. G. Gencer, C. Besikci, 2010, "Thermal Images of Electrically Stimulated Breast: a simulation study," International Medicon 2010 12th Mediterrenean Conference.

H. F. Carlak, N. G. Gencer, C. Besikci, 2011, "Medical Thermal Imaging of Electrically Stimulated Woman Breast:a simulation study," Engineering in Medicine and Biology Society, EMBC, 2011 Annual International Conference of the IEEE, IEEE, Aug. 30, 2011, pp. 4905-4908.

G. Qiao, W. Wang, L. Wang, Y. He, B. Bramer and M. Al Akaidi, 2007, "Investigation of Biological Phantoms for 2D and 3D Breast EIT Images," IFMBE Proceedings 17, pp. 328-331.

Y. Arslan, 2009, "Large Format Dual-Band Quantum Well Infrared Photodetector Focal Plane Arrays," Metu, M.Sc. Thesis, Chapter 1.

* cited by examiner

METHOD AND SYSTEM FOR DUAL-BAND ACTIVE THERMAL IMAGING USING MULTI-FREQUENCY CURRENTS

BACKGROUND OF THE INVENTION

The present invention is mainly concentrated on the diagnosis of the breast carcinoma using a hybrid technique incorporating both thermal and electrical impedance imaging methods. The innovation of the approach relies on the frequency dependence of the tissue's electrical impedance which facilitates the acquisition of multiple thermal images with currents at different frequencies injected to the region of the body under inspection. This new technique improves the sensitivity of medical imaging over the standard thermography as follows.

Current injection at a single frequency increases the temperature gradients in the unhealthy regions enhancing the visibility (detection probability) of the cancerous tissues with a thermal camera, Current injection at multiple frequencies along with thermal imaging with a thermal camera results in generation of multiple thermal images according to the frequency dependencies of the tissue conductivities since heat generation (measured by the thermal camera) due to current injection is related with the tissue conductivity.

As a result, the technique allows the acquisition of the frequency dependent tissue conductivity distribution along with enhanced temperature gradients in the body regions with unhealthy tissues which, when interpreted simultaneously, are expected to considerably increase the sensitivity of medical thermal imaging.

The invention can be used in all clinical applications of the thermal imagers:
- oncology (breast, skin, etc.),
- pain management control,
- vascular disorders,
- arthritis/rheumatism.
- neurology,
- surgery (open heart, transplant, etc.),
- ophthalmic. (cataract removal),
- tissue viability,
- thyroid (diagnosis and treatment),
- dentistry,
- monitoring efficacy of drugs and therapies,
- respiratory (allergies, SARS),
- sports and rehabilitation medicine.

PRIOR ART ABOUT THE INVENTION (PREVIOUS TECHNIQUE)

Various imaging modalities are used for diagnostic purposes and monitoring the treatment processes. These modalities provide images of different physical properties of the body tissues. Table 1 shows a list of these modalities and corresponding physical properties:

TABLE 1

Medical Imaging Methods and Corresponding Physical Properties

| Imaging Method | Physical Property |
| --- | --- |
| X-ray Computerized Tomography | Attenuation coefficient |
| Ultrasound | Reflection coefficient |
| Magnetic Resonance Imaging | Proton density, transverse and longitudinal decay constant |
| Nuclear Techniques (PET) | Capacity of holding radioactive materials |
| Electrical Impedance Imaging | Electrical Impedance |
| Infrared Thermal Imaging | Emissivity and temperature distribution |

For the diagnosis of breast carcinoma, mammography is the standard test for breast screening. However, this method has accuracy problems especially for smaller tumors and it is not comfortable for patients since the breast needs to be squeezed to minimize the path length between source and detector. If the dimension of a tumor is lower than 1.6 cm, it cannot be reliably sensed by this technique, since X-rays passing through the tumor are not detectable. Statistical studies show that there 10-25% false negative (tumor is not detected following a mammogram) ratio in mammography. Another concern is the exposure of the patient to ionizing radiation (X-ray) which is potentially harmful for the human tissue.

Ultrasound is another important imaging method that is used to evaluate the breast. However, this technique is not successful in detecting micro formations and monitoring deep regions of the breast.

Magnetic resonance imaging (MRI) is another imaging modality used in breast imaging. However, it should be used as a complementary tool instead of utilizing as a self-sufficient screening tool. Although it is more sensitive than mammography, it has a higher false-positive rate which may result in unnecessary biopsies. At the same time, due to the relatively long data acquisition time, this technique is not the first choice by the patients. Currently, there is no gold standard in detecting cancerous tissue in the breast. To minimize diagnostic errors, multi-modal techniques are proposed that employ more than one technique to complement each other.

Now imaging techniques have also been investigated. Electrical Impedance Tomography (EIT) and Infrared Thermal Imaging (origins of this invention) were developed for this purpose. However, these techniques are not also sufficient as a sole screening tool. They have been used as an adjunct to the conventional medical imaging techniques.

In EIT, changes in the electrical properties of the tissues are used in the diagnosis of breast cancer. However, in EIT applications, the current applied on the surface of the tissue has the highest intensity beneath the current drive electrodes. When the electric current is applied from the surface, the current cannot be focused homogeneously in the desired body location. Therefore, desired amount of signal cannot be provided from the inner regions of the body. In addition, the number of measurements are limited by the number of current drive electrodes. This results in low-resolution images. To enhance the signal strength, the current intensity can be increased; however, the applied current should be below the medical safety limits. One way to improve the resolution is to increase the number of electrodes. However, this requires a more demanding hardware, since the signal level decreases and the interaction between the electrodes increases.

Thermal imaging is another technique that may be used to screen breast cancer, it also gives complementary information about developing cancerous tissues. Abnormal breast thermogram shows a significant risk indicator for the breast cancer. Several studies report infrared imaging as an important risk marker. Thermal imaging gives information about metabolic activity and tumor induced angiogenesis instead of structural knowledge such as size of the tumor and micro calcifications. Infrared imaging may also show indications almost 10 years before the development of breast cancer, unlike other imaging modalities. When this important ability combines with its proven high specificity and sensitivity rates, thermal infrared imaging becomes an invaluable tool in breast cancer diagnosis.

In thermal imaging, the radiation emitted from infrared region of the electromagnetic spectrum is measured by an infrared thermal imaging camera and temperature distributions corresponding to the measured thermal emission are displayed. Infrared imaging is the only imaging modality which can image the metabolic aspect of the breast. Thermal image is an indicator of abnormal pathophysiology and physiology.

Thermal Imaging provides images related to two different physical properties of the tissue: temperature and emissivity. The method has the following properties:
generates surface images instead of tomographic image,
can be used as real-time imaging modality,
portable,
relatively inexpensive,
relies on continuous investment for its development, based on other important uses (for industrial, military, and space research)
it has no harmful effect on the human body due to the passive mode of operation,
offers contactless and non-invasive imaging (no contact with the patient).

Diagnostic capabilities of the method vary depending on the rumor size and the distance to the surface. In the early stages of the disease, diagnosis of smaller tumors is limited, especially for distant masses from the surface.

Nyirjesy and associates implemented a study which compares the accuracy of clinical examination, thermography and mammography in the breast cancer detection. 16778 patients were participated in that study. There were 8757 asymptomatic patient, 4715 confirmed carcinoma patients and 3305 histologically diagnosed benign breast cancerous patients. In that study, the diagnostic performances of a mammography, thermography and clinical examination results are summarized (Table 2).

TABLE 2

Accuracy rates of different methods in the diagnosis of breast cancer (Nyirjesy 1986).

|  | Specificity (%) | Sensitivity (%) |
| --- | --- | --- |
| Mammography | 73 | 80 |
| Thermography | 85 | 88 |
| Clinical examination |  | 75 |

In Thomassin et al. study, 130 malignant tumors ranging in diameter 3-5 mm were detected out of 4000 confirmed breast cancer cases. 10% of them were diagnosed by mammography, 50% of the patients were diagnosed by thermography and rest of them which could not be detected either mammography or thermography were diagnosed (40%) by multi modal imaging (mammography and thermography). As a result, many studies were reported that abnormal breast thermogram shows a significant risk indicator for the breast cancer.

Infrared thermal imaging system can obtain high spatial resolution thermal images of the tissue without contact. Although it has higher sensitivity and specificity, smaller cancerous tissues cannot be detected from deeper locations since the temperature contrast on the breast surface due to metabolic heat generation of the cancerous tissue may not be sufficient to be sensed. Tumor tissue cannot produce adequate amount of temperature difference on the skin surface. While, the noise equivalent temperature difference (NETD) of the state-of-the-art thermal infrared cameras is as low as several mK, detection may not be possible especially for smaller tumors located at deeper regions. The thermal sensitivity can be increased by developments in the detector technology, but this requires a high cost and long-lasting R&D work.

A. W. Guy implemented an active thermographic study with tissue mimicking phantoms. In that study, electromagnetic fields at different frequencies are applied by various microwave sources as plane wave, aperture, slot and dipole sources, and the heating pattern is observed due to the electric field.

M. Mital and E. P. Scott have studied on the diagnosis of embedded tumors with an infrared camera. They placed a heat source in a cylindrical biological phantom and imaged the temperature distribution on the phantom surface. The heater (resistance 32Ω) was embedded in the agar to simulate the tumor tissue's temperature increase. Power dissipation of the heat source was adjusted by changing the voltage of the heater. Infrared camera had 80 mK thermal resolution and the emissivity of the agar phantom (1% solution of agar) was 0.97. Genetic algorithm was implemented to be able to determine the heat generation rate and location of the source from the temperature distributions.

F. J. Gonzalez presented a thermal simulation study of breast tumors. Woman breast was modeled with as 9 cm radius hemisphere and the spherical model of the tumor tissue was embedded in it. In that study, the smallest size of cancerous tissue is explored for each depth using state-of-the-art thermal infrared cameras. The results showed that 3 cm tumors can be detected from 7 cm depths and smaller tumors can be diagnosed if they are located closer to the skin surface.

L. Jiang et. al. conducted simulation study on the thermography of the woman breast under elastic deformation. They modeled the woman breast by taking the gravity-induced elastic deformation into account. This was the first study adding this parameter beside the metabolic, heat generation, blood perfusion, thermal and electrical boundary conditions, and thermal and electrical conductivities of breast tissue. Numerical breast models were developed using the 3D finite element method by including the thermal and elastic properties of the breast tissue. Temperature differences due to tumor tissue were obtained numerically for both static and dynamic thermal states. The developed modeling technique establishes a connection between breast thermography and pathological and physiological factors due to cancerous tissue.

Most of the clinicians and radiologists are well experienced on the structural anatomy and medical education but they are not experts on thermodynamics, thermokinetics and physical and biological basis of infrared imaging. This may appear as a problem for the effective utilization of thermography for medical imaging. However, technological developments in digital processing, image acquisition and user friendly software facilitate the use of infrared imaging. Multispectral images could be obtained with the improvements in narrow-band filtering. With dual band thermal cameras, two different images for the same body can be acquired at different wavelengths. Software advances in smart processing (artificial intelligence) make the post image processing of raw data possible. Artificial neural networks, automated target recognition and threshold algorithms are the most commonly used ones. Data summation is used in artificial neural network algorithm to obtain pattern recognition. On the other hand, threshold and automated target recognition algorithms use a normative data base. These improvements have raised the accuracy of the system and have reduced the need for skillful operators.

A period of heating and then cooling was proposed (e.g. with the aid of the fan) in order to improve the diagnostic performance (Keyserlingk, 2000; Ohashi, 2000). Kachzmarek and Nowakowski (2004) proposed optical heating of tissues in the IR band. Arabi and Muttan (2008) have applied both optical and microwave energy for this purpose. Such non-destructive testing methods which are used in industry is called the active dynamic thermography, while different energy types are applied for this purpose (electromagnetic, vibration with ultrasound, laser, hot air, or microwave). The terminology of Active Dynamic Thermography is relatively new in the medical imaging literature.

Cyril Smith's patent, named as Thermal Imaging using Electro-Magnetic Induction, is on active mode operation of thermal infrared cameras. In this study, the aim is determining the hidden and embedded objects in the environment (suitcases, soil, etc.) by thermal infrared camera with higher performance.

System is based on,
high-frequency (1-2 GHz) electromagnetic waves applied to the body,
electromagnetic waves radiated from the body.
interference pattern formed on an electrically conductive layer.

In this method, a resistive metal layer is placed in front of a thermal camera. Thermal camera continuously displays the temperature distribution on this layer. Time-varying current (1-2 GHz) is applied in short time periods into the coil placed behind a layer. Magnetic fields created by the coil induce current in conductive objects, and magnetic fields created by the induced currents change the current distribution on the metal layer and therefore the temperature distribution. Hidden/buried object can be determined in a wide area by changing the position of the camera/metal sheet/coil assembly. This system has no clinical application.

Zombo et. al. developed a system, named as "Hand held magnetic induction thermography system". By moving a coil/IR camera system manually, the object to be displayed is scanned. Eddy-currents are induced in the object with the 100-1000V, 10-100 A current (10-1000 kHz) injected to the coil. Current and temperature distribution change in the defective areas of the material. This difference can be distinguished in the thermal images, and error location can be determined. Different current distributions in the object can be obtained by changing the coil axis, and the image contrast can be changed. No medical application was predicted.

Herbert L. Berman and colleagues proposed an active thermographic system which is described in the patent US 2007/0213617 A1. The idea of this patent is based on the study of Kachzmarek and Nowakowski's (2004) optical heating of tissues. Breast tissue is heated by a halogen lamp (optic stimulation) for 30 seconds from 50 cm distance. In that study, this topic is embedded into various innovative ideas (dual-band imaging, the contact of the breast with the glass which is transparent to infrared wavelengths, heating with heater or it is the only active thermographic system which has a medical application. The additional temperature in the tissue is generated by the light applied from the surface. Another system, namely, "Infrared Defect Detection via Broad-Band Acoustics" was patented by Raulerson and etc. In this study, heating the object with wide-band (1 kHz-1 MHz or 10 kHz to 50 kHz) acoustic energy was proposed to improve the performance for industrial applications of thermal cameras (e.g. fault finding equipment).

It is possible to access a large number of patents about active thermography, however, they refer to methods for different industrial applications and signal processing methods. The only patent that refers to medical applications is the Berman and colleagues' patent which was taken in 2007 where active thermography was implemented using halogen light sources.

In the present invention, external energy is applied to the body in a different manner. Electrical current is applied from the surface with electrodes yielding an additional heat source in the tissue. Since electrical conductivity and permittivity of tissue alter with frequency; multi-frequency current application provides a means to image electrical properties for different frequencies by measuring different temperature distributions on the body surface. Therefore, the technique is expected to be able to detect anomalies in terms of both temperature and tissue conductivity differences as may be displayed by the breast carcinoma.

In 2009, Carlak et. al. showed that low frequency electrical currents applied from the surface provide significant performance improvements in the breast cancer diagnosis. In that study, simulation of a 2-dimensional electrical conductivity model of the breast slice was implemented, and it was shown that a 1 cm tumor located 4.5 cm away from the electrodes can be distinguished with the state of the art thermal imagers.

In 2010, the same group was conducted a similar study with a 3-dimensional (cube-shaped) electrical conductivity breast model. It was shown that operating at a frequency of 10 kHz, a 40 $cm^3$ tumor in the breast tissue (heated 300 seconds) can be distinguished from a 1.5 cm depth from the surface at the axis of the camera.

SUMMARY OF THE INVENTION

Invention is about a hybrid technique that incorporates thermal and electrical imaging methods for the diagnosis of cancerous tissues. In this system there are three main ideas:
Using the electrical properties of the tissue for diagnostic aims,
Obtaining different information/different images depending on the operation frequency of the applied current,
Imaging the surface temperature and emissivity parameters by measuring the infrared emission.

Proposed method without current application (i.e., in passive mode of operation) provides images which are obtained by standard thermal imaging systems. However, when the electrical current is applied (in active mode of operation) the temperature contrast on the surface changes depending on the electrical properties of the tissue. Electrical current density below the medical safety limits is applied to the patient for this purpose.

Since tissues exhibit different electrical properties, it is possible to obtain useful information on the anatomy of the human body and tissues' health status by imaging, for example, the electrical conductivity distribution of the tissues. These images can be used to identify organs and evaluate their health status. The method, for example, can be employed to detect breast carcinoma. Table 3 shows the conductivity properties of several types of breast tissues for different operation frequencies. Note the relative change and the contrast between the tumor tissue and healthy breast tissue conductivities at different frequencies.

TABLE 3

Electrical conductivity (mS/cm) values of breast tissues at different frequencies

| Breast Tissue | 10 kHz | 100 kHz | 10 MHz |
|---|---|---|---|
| Tumor (center) | 3.98 | 4.28 | 7.24 |
| Tumor (surrounding tissue) | 1.62 | 1.70 | 2.70 |
| Fatty with tumor cells | 0.65 | 0.67 | 1.08 |
| Tissue far from tumor center | 0.28 | 0.31 | 0.37 |
| Healthy breast tissue | 0.22 | 0.22 | 0.25 |

Since the electrical conductivity and permittivity of the tissues change with frequency different images can be reconstructed for each operation frequency yielding more than one image for the same body. The time course of the temperature distribution is recorded using thermal infrared cameras. The resultant images are a function of electrical and thermal properties of the tissues and may provide valuable diagnostic information.

This method utilizes the enhancement in the temperature difference generated by the cancerous tissue formation by current injection through surface electrodes placed on the inspected region of the body, tissue conductivity imaging by thermography using the dependence of the heat generation on the tissue conductivity, the different frequency dependencies of the cancerous (strong dependence) and healthy (weak dependence) tissues in a properly selected frequency interval.

The technique enhances the temperature difference generated by cancerous tissue by injecting currents within safety limits to the inspected region of the body as well as measuring the conductivity distribution through thermal imaging. Comparison of the conductivity distribution data obtained through current injection at different frequencies yields information on the presence/absence and location of possible cancerous tissues in the body.

In order to increase the sensitivity of the technique, a thermal camera with dual band (MWIR/LWIR) imaging capability is utilized. For this purpose, the dual band camera includes a single sensor capable of imaging in both bands (MWIR and LWIR). Due to the low cost and the narrow band spectral response nature of the Quantum Well Infrared Photodetector (QWIP) technology, a dual band MWIR/LWIR QWIP seems to be feasible for this approach although detectors based on the HgCdTe, Type II superlattice and quantum dot infrared photodetector (QDIP) technology can also be utilized. The thermal image is first recorded in the MWIR (3-5 (m) band and then in the LWIR (8-12 (m) window in two different wavelength intervals centered around (1 and (2. The ratio of the spectral exitances ($M_O$) of two blackbodies at these wavelengths can be expressed by the following equation $$\frac{M_\lambda(\lambda_1)}{M_\lambda(\lambda_2)} = \frac{\lambda_2^5 \left(e^{\frac{hc}{\lambda_2 k_B T_{obj}}} - 1\right)}{\lambda_1^5 \left(e^{\frac{hc}{\lambda_1 k_B T_{obj}}} - 1\right)}$$

where $T_{obj}$ is the temperature to be measured, h is the Planck's constant, $k_B$ is the Boltzmann constant, and c is the speed of the light. Therefore, the temperature can be measured accurately by a dual band sensor if the emissivity of the object does not significantly change between these wavelength intervals. The other advantage of utilizing dual band imaging is benefiting from the individual advantages of both MWIR and LWIR bands for medical imaging as well as the possibility of thermal imaging performance enhancement by processing the image data obtained in two different thermal imaging bands. In order to facilitate all of the above possibilities, the dual band camera should be able to operate in the following modes selectable by the operator;

i. single band imaging mode in the MWIR window
  ii. single band imaging mode in the LWIR window
  iii. dual band imaging mode in the MWIR and LWIR windows In the third (iii) mode two alternatives are possible. The camera can yield image data in both windows (MWIR and LWIR) simultaneously or sequentially on a frame by frame basis in which case one frame containing the image data in one window will follow the other.

The infrared sensor can be of mid (such as 320×256 and similar formats) or large (such as 640×512 and similar formats) format while lower formats with degraded resolution or higher formats with increased cost are also possible.

AIMS FOR THE DEVELOPMENT OF THE INVENTION

The aims for the development of the medical electro-thermal imaging method and the system thereof, are;

Procuring an imaging system without using ionizing radiation which is potentially harmful for the human health, Developing a method that can detect and define the tumor type in the same examination process, Developing a system that can detect the tumors in deeper areas of the tissue, and the micro calcifications in the tissue, Obtaining a comfortable examining procedure, which has relatively short diagnosing time, The advantages of the invention over the current technology and other thermal imaging methods can be summarized as follows:

Using three physical properties of the tissue, thermal properties, emissivity property and electrical properties (electrical conductivity and permittivity and possibly magnetic permeability), for more reliable imaging of the examining area over the passive thermography which uses two physical property of the tissue, thermal and emissivity properties, Comfortable electric current insertion using surface electrodes instead of embedded electrodes, Applying electric current normal to the surface using electrodes to obtain better resolution in the normal direction, Attainability of different thermal images of the area regarding to the form and the number and configuration of the electrodes, Achieving high resolution images using dual band (MWIR and LWIR) active thermography, Easy reconfiguration of the location of the electrodes during examination, Obtaining as many thermal images as the inserted electric current frequency variety for obtaining larger amount of data in order to increase the reliability of the assessment, The advantages of the invention over other active thermography methods:

Since the electrical current is applied from the surface of the material (tissue), it can be penetrated vertically in the tissue. By applying electrical currents, higher temperature contrast can be provided at deeper regions.

In the invention, it is possible to change the number, position and shape of the electrodes easily. When the electrodes are located closer to the tumor, the current density increases in the tumor region, and the temperature contrast on the surface gets higher.

In passive thermography methods, electrical properties of tissues are not expected to considerably affect the thermal images. On the other hand, active thermography method (with the electrical current application) creates thermal images (temperature distributions) depending on the electrical properties of tissues (electrical conductivity, electrical permittivity and possibly magnetic permeability). Since these features vary with the injected current frequency in the tissue, different temperature distributions can be obtained correspondingly.

Applying current increases the temperature contrast.

By using dual-band infrared camera, two separate images in two different wavelength intervals can be obtained for a frequency value of the applied current. These images may have different details according to each other and the individual advantages of single band MWIR and LWIR imaging can be combined in this way. At the same time, skin temperature can be measured much more reliably when compared with single band imaging as explained above. Harold Szu has a patent on dual-band infrared camera usage in medical imaging. However, dual-band infrared thermal imaging with the method proposed in our invention has not been implemented yet.

Technical Problems Solved by the Invention

As mentioned above, decrease in the thermal contrast depending on the tumor depth is the fundamental problem of the passive thermography systems. The diagnostic performance of the passive thermography systems is not sufficient especially for smaller tumors located at deeper regions. This problem is solved by the present invention.

Our numerical analysis show that 1.5 mm tumors, smaller than the critical tumor size (2-3 mm), can only be detected by passive thermography from 3 mm depth. On the other hand, by using the active thermography method, mentioned in the invention, the same tumor can be detected from 1 cm depth from the breast surface. If the tumor size enlarges to 3.5 mm, cancerous tissue at 1.5 cm depth generates more than 20 mK temperature contrast on the breast surface and can be sensed with the state-of-the-art thermal imagers by using active thermography.

The Differences of the Invention (from the Other Known Imaging Modalities)

Invention, a hybrid modality, is the combination of electrical impedance imaging with thermal infrared imaging which we name Medical Electro-Thermal Imaging. This new functional imaging modality utilizes both techniques and minimizes individual drawbacks of these two imaging systems. Based on the innovations mentioned above, imaging performance is expected to be improved by increasing the sensitivity and specificity of EIT and Infrared Imaging Systems. This attribute has not been existed in any imaging modality. The invention is based on the idea that tissue electrical properties, which contain important information for the diagnosis, affect the temperature distribution and this effect can be acquired via contactless measurements. For this purpose, the current is applied to the patient within medical safety limits, and the temperature distribution depending on the electrical properties is measured using an infrared thermal camera.

DESCRIPTIONS OF FIGURES

The names of the drawings presented for better understanding of medical electro-thermal imaging method and the system thereof are listed as follows.

The numerals referred to in the following description correspond to the following,
1. Infrared camera,
2. Electrodes,
3. Cancerous tissue (tumor),
4. Breast tissue,
5. Control unit,
6. Current source,
7. Surface of the breast tissue,
8. Thermal image.

DETAILED DESCRIPTION OF THE INVENTION

Theory

Figure 4:
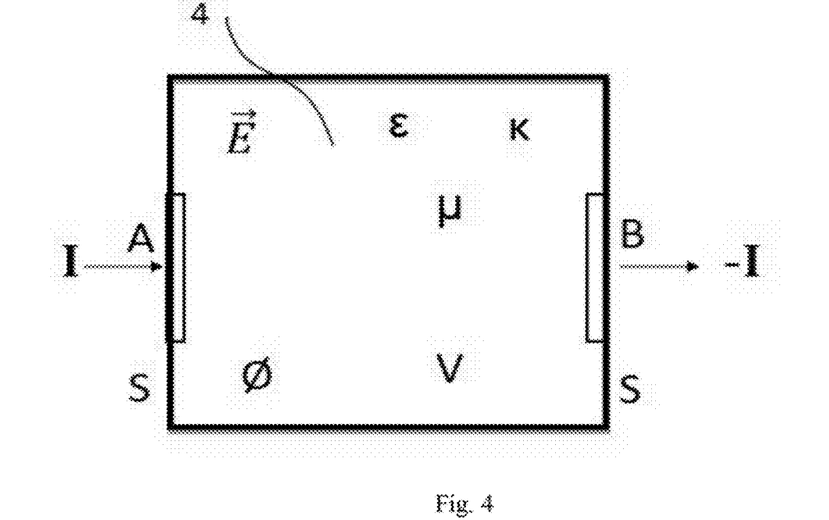
FIG. 4. Electromagnetic model of the tissue exposed to the electric current.

We present below the theoretical analysis of thermal contrast enhancement with current injection. Electromagnetic problem of the method is modeled and the schematic of the electromagnetic problem is shown in FIG. 4. The electrical model of the body is represented using permeability $\mu = \mu_0$, electrical conductivity $\kappa$ and permittivity $\in$. Sinusoidal currents are applied using two electrodes attached on the body surface at points A and B. Applied currents generate an electric field in the conductive body. The steady-state electric field $\vec{E} = -jw\vec{A} - \nabla \varnothing$ can be calculated using the following coupled partial differential equations, $$\nabla^2 \vec{A} - jw\mu(\kappa + jw\in)\vec{A} - \mu(\kappa + jw\in)\nabla\varnothing = 0$$

$$\nabla \cdot [(\kappa + jw\in)\nabla\varnothing] + \nabla(\kappa + jw\in) \cdot jw\vec{A} = 0$$

and boundary conditions $$\kappa \frac{\partial \varnothing}{\partial n} = \begin{cases} I \text{ on } A \\ -I \text{ on } B \\ 0 \text{ otherwise} \end{cases}$$

where $\vec{A}$ is the magnetic vector potential, Ø is the scalar potential, and I is the current applied from the surface.

Figure 5:
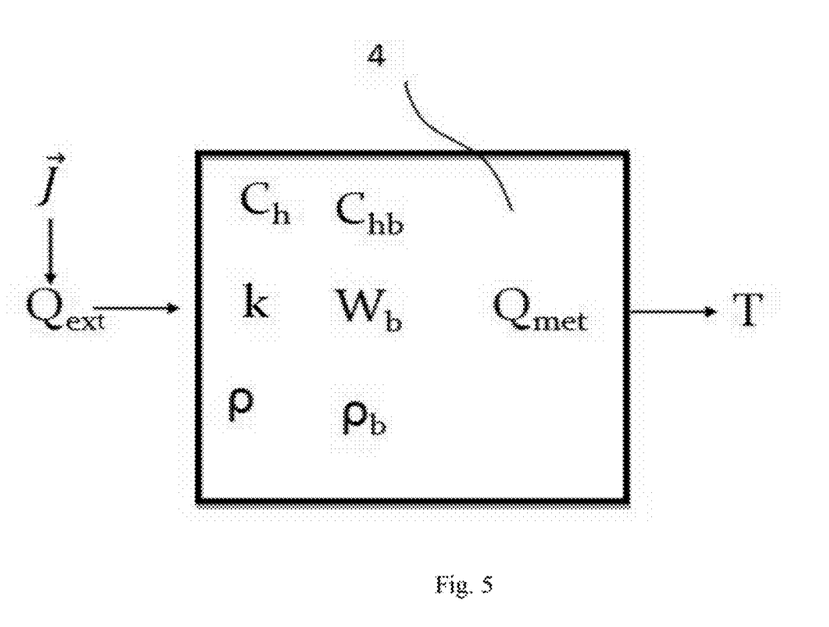
FIG. 5. Thermal model of the tissue.

Thermal problem is also modeled to obtain the temperature distribution inside the tissue. Schematic of the Bio-Heat problem (including an external heat source due to current application) is shown in FIG. 5. Pennes Bio Heat Equation is used to describe the effects of metabolic generation and blood perfusion over the energy balance. It explains the thermal interaction between tissues and perfused blood in detail:

$$\rho C_h \frac{\partial T}{\partial t} + \nabla \cdot (-k \nabla T) = Q_b + Q_{met}$$

where, $\rho$ is the density (kg/m³), $C_h$ is the specific heat (J/kgK), T is the absolute temperature (K), k is thermal conductivity (W/mK), $Q_b$ is the heat source due to blood perfusion and $Q_{met}$ is the metabolic heat generation (W/m³).

The first term on the right hand side is the source due to blood perfusion which can be expressed as $$Q_b = \rho_b C_{hb} W_b (T_b - T)$$

where, $\rho_b$ is blood mass density (kg/m³), $C_{hb}$ is the blood specific heat rate (J/kgK), $W_b$ is the blood perfusion rate (1/s), and $T_b$ is the blood temperature (K) which is approximated to the core temperature of the body, and the temperature of the venous blood is approximated to T which is the unknown temperature value (local tissue temperature (K)).

Law of conservation of energy states that the heat lost from the skin surface is in a constant equilibrium with the heat supplied by the vascular flow to the skin in the steady state. Thus, heat transfer from the front skin surface (by both convection and radiation to the surrounding air and surfaces at specified temperatures) should be considered as the boundary conditions:

$$Q_{conv} = h_h A_s (T_S - T_\infty)$$

$$Q_{rad} = e \sigma A_s (T_s^4 - T_{sur}^4)$$

where, $h_h$ is the convection heat transfer coefficient (W/m².K), $A_s$ is the surface area through which the convection heat transfer takes place, $T_s$ is the surface temperature, $T_\infty$ is the temperature of the air, e is the emissivity of a skin (0.95), $\sigma$ is the Stefan-Boltzmann constant (W/m². K⁴), and $T_{sur}$ is the temperature of the walls, ceiling and floor. In this study, $T_{sur}$ is assumed to be equal to the air temperature ($T_{sur} = T_\infty$).

Note that, the boundary condition at the front skin surface can also be written as:

$$-k \nabla T = h_h (T - T_\infty)$$

Here, $h_h$ (W/m²K) represents the overall heat transfer coefficient due to the combined effect of radiation and convection.

To set the boundary condition at the rear surface of the breast, the temperature of the thoracic wall can be assumed to be the core temperature of the body (i.e., 310 K).

Due to the applied external current sources, a new term should be added to the right-hand side of the Pennes Bio Heat equation:

$$\rho C \frac{\partial T}{\partial t} + \nabla \cdot (-k \nabla T) = Q_b + Q_{met} + Q_{ext}$$

The external heat term $Q_{ext}$ is calculated using the following Joule Heat Equation:

$$Q_{ext} = \frac{1}{\kappa} |J|^2$$

where J is the electrical current density and $\kappa$ is the electrical conductivity of the tissue.

Medical electro-thermal imaging method comprises the steps of, a. Preparation of the patient and the imaging room according to the thermal imaging standards, b. Recording the passive mode thermal image(s) of the body in two different windows (MWIR and LWIR) using dual band infrared camera (1), c. Selecting the frequency of electric current that is attached to the breast tissue (4) using control unit (5), d. Placing the electrodes to the previously specified locations on the surface of the breast tissue (4), e. Applying the electric current for predetermined time period to the targeted breast tissue (4), f. Recording the active thermal image (8) of the stimulated area (in both bands (MWIR and LWIR)) in the heating period, g. Recording the active thermal image (8) of the stimulated area (in both bands (MWIR and LWIR)) in the cooling period until the temperature of the breast tissue (4) becomes stable, h. Going to the item c and repeating the same procedure for different frequency values of the applied electric current, i. Eliminating position differences of the active (8) and passive thermal images and making necessary matching processes (image registration), j. Obtaining the absolute temperature value of the breast and cancerous tissue (3 & 4) using the dual band property of the thermal camera (1), k. Comparing and determining the ratio/difference of the active (8) and passive thermal images obtained under different frequencies using the image processing algorithm which is embedded to the control unit to detect the cancerous tissue (3), l. Carrying out steps c through k until a healthy diagnosis or detection is made.

Figure 1:
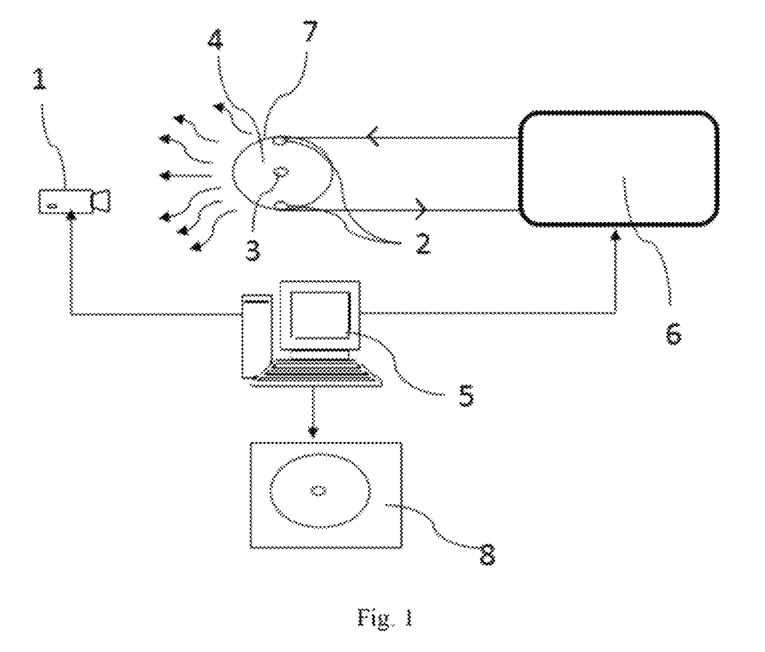
FIG. 1. Schematic view of the medical electro-thermal imaging system
Figure 2:
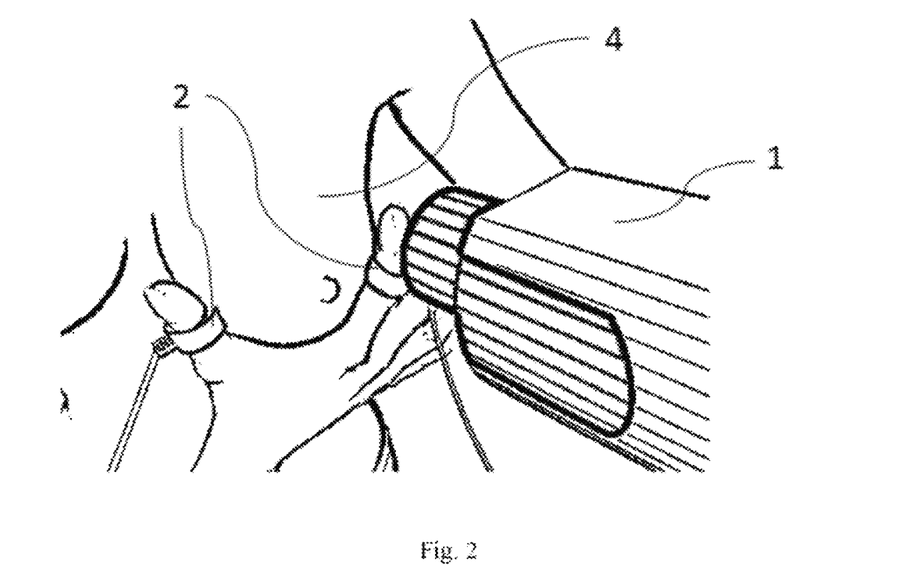
FIG. 2. Application of the medical electro-thermal imaging method using the medical electro-thermal imaging system.
Figure 3:
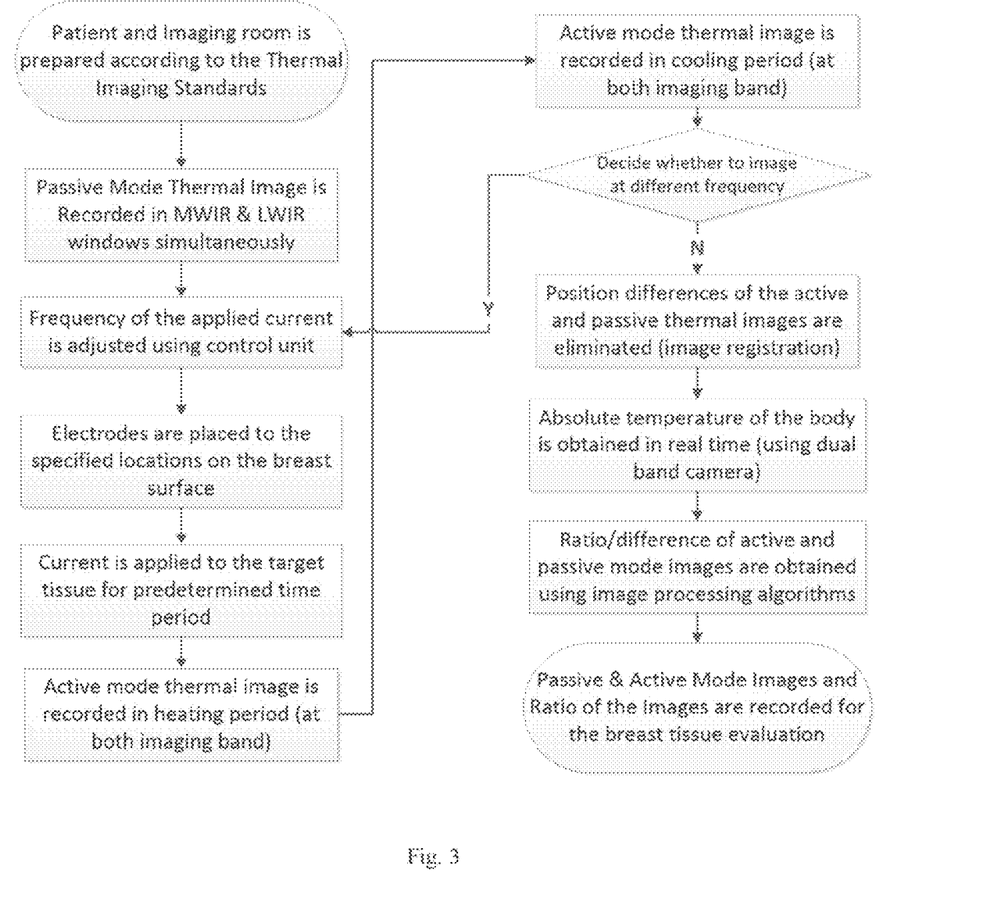
FIG. 3. Flow chart of the medical electro-thermal imaging method.
Figure 6:
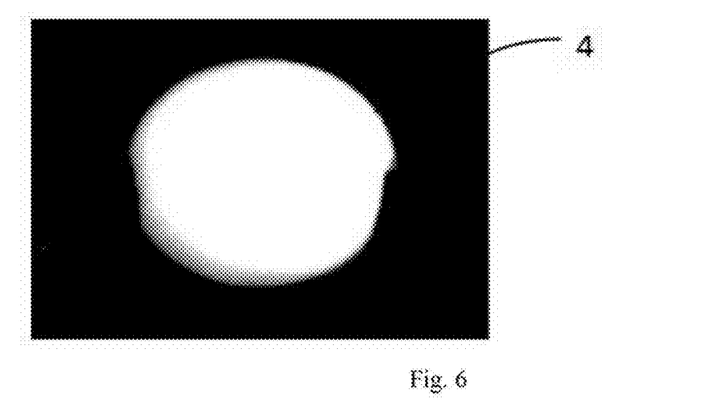
FIG. 6. Temperature distribution of the healthy and the tumor tissue (realistic breast phantom) taken in passive mode.
Figure 7:
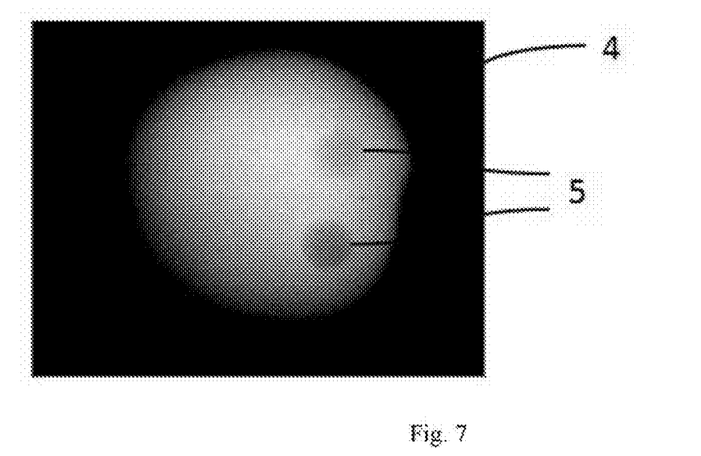
FIG. 7. Ratio of thermal images taken in active and passive mode.
Figure 8:
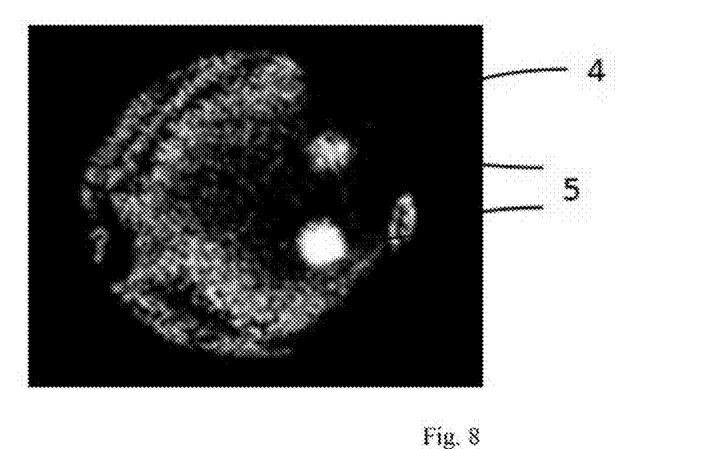
FIG. 8. Image showing the difference of healthy tissue and tumor in active mode of operation.

The proposed hybrid imaging method is denoted in FIG. 1. FIG. 2 shows the application of the system in practice. In this imaging method, electrical current within medical safety limits is applied to the breast tissue from the surface, by means of electrodes (2) placed on the fingers. The temperature distribution on the breast surface (4) is recorded in real time with an infrared camera (1). Due to the current application, the presence of tumor in the breast causes higher temperature contrast on the breast surface. This temperature difference is determined in the thermal image (8) obtained by the infrared camera (1). FIGS. 6, 7, and 8 are thermal images of the realistic breast phantoms which mimic the healthy and cancerous breast tissue. These thermal images were obtained using a QWIP single band (LWIR band) thermal infrared camera.

The preparation of the room and patient according to thermal imaging standards is an essential part of the medical electro-thermal imaging method for making correct diagnosis about the breast tissue. Imaging should be implemented in a controlled manner. Patients disrobe to the waist and let the surface of the breasts to cool to room temperature (18-22° C.) for 10-15 minutes.

After the preparation procedure is completed, passive thermal image of the tissue is recorded. In this passive mode, since there are no external sources, the camera displays the surface radiance distribution due to the internal sources (metabolic heat generation and blood fusion). The passive thermal image is used for the comparison with an active thermal image (8) which is obtained after the medical electro-thermal imaging method is applied. The passive thermal image of the target area is given in the FIG. 6.

After placement of the electrodes, the current is injected to the breast tissue (4). Since electrodes (2) are non-invasive type, there is no need for the insertion of the electrodes into the tissue. Electric current is injected from the surface of the breast tissue (7). The electric current is applied to the tissue (4) until the temperature of the tissue (4) become stable or along predetermined period and then active thermal image (8) is recorded using an infrared camera (1).

Dual band sensor usage yields to measure the absolute temperature. Thermal imaging performance is improved by processing the images which are obtained in two different thermal imaging bands (MWIR and LWIR bands).

Different thermal images can be recorded for different electrode locations. If the places of electrodes (2) are changed with respect to the location of the tumor tissue (3) higher temperature contrasts may be achieved by moving the electrodes (2).

The parameters that affect the temperature contrast are the tumor dimension, amplitude, duration and frequency of the stimulation current, and location (depth) of the tumor tissue. Increasing the strength of the applied current causes higher contrast in the thermal images. Tumor dimension is also another important parameter affecting the temperature contrast. As the size of the tumor increases, higher temperature contrasts are obtained, and consequently, they can be diagnosed from deeper regions of the breast. An example to the ratio of passive and active (8) thermal images in other words contrast of the active (8) and passive thermal images given m the FIG. 7, and ratio of the healthy (8) and the tumor tissue (8) which are taken in active mode of operation is given in the FIG. 8.

Medical electro-thermal imaging system comprises;

Infrared camera (1) which can display temperature distribution in the focused area, Electrodes (2) that drive electric current to the breast tissue (4), Control unit (5) that regulates the electric current provided by current source (6), that records image by the data provided by infrared camera (1) and makes comparison between the passive and active thermal images (8).

Current source (6) which provides the electric current that is inserted to the breast tissue (4).

The invention claimed is:

1. A medical electro-thermal imaging method, comprising the steps of:
   a. preparing a patient and the imaging room according to a thermal imaging standards;
   b. recording of a passive thermal image of the tissue in two different windows (MWIR and LWIR) using a dual band thermal camera;
   c. placing a plurality of non-invasive electrodes to the specified locations on the surface of the breast tissue;
   d. selecting frequency of an electric current that is inserted to the breast tissue using the control unit;
   e. applying the electric current to the targeted breast tissue for predetermined time period;
   f. recording an active thermal image of the stimulated area in, heating period (in both windows (MWIR and LWIR));
   g. recording the active thermal image of the stimulated area in cooling period (in both windows (MWIR and LWIR)) until the temperature of the breast tissue becomes stable;
   h. going to the item c and repeating the same procedure for different frequency values of the applied electric current;
   i. eliminating the position differences of the active thermal image and the passive thermal image and matching the active thermal image and the passive thermal image (image registration);
   j. obtaining the absolute temperature value of the breast and cancerous tissue for any screening time period using the dual band property of the thermal camera;
   k. comparing and determining the ratio/difference of the active thermal image and the passive thermal image (in single band and dual band imaging modes) obtained under different frequencies using the image processing algorithm which is embedded in the control unit to detect the cancerous tissue (tumor tissue);
   l. if the active thermal image is not enough to make a healthy diagnosis for the presence of the tumor after changing the frequency of the electric current or the positions of the electrodes; carrying out the previous d, e, f, g, h, i, j, k and l steps until a healthy diagnosis or detection is made;
   wherein the decision in this sense is made with the help of the algorithm embedded in the control unit; and
   wherein the patients disrobe to the waist and let the surface of the breasts cool to room temperature of 18-22° C. for 10-15 minutes.

2. A medical electro-thermal imaging system configured to perform the method of claim 1, which uses the electric current as an external heat source to improve the temperature contrast, comprising:
   an imaging room configured to satisfy the thermal imaging standards;
   a dual-band infrared camera configured to sense temperature emission and emissivity of the focused area to record a passive and an active thermal image of the tissue in two different windows (MWIR and LWIR);
   a plurality of non-invasive electrodes are configured to insert the specified locations on the surface of the breast tissue deliver the electric current to the breast tissue;
   a voltage controlled current source configured to provide the electric current that is injected to the breast tissue;
   a control unit configured to regulate the alternating electric current that is provided by the current source to record image by the data provided by infrared camera to make image registration by eliminating the position differences of the active and passive thermal image and match the active thermal image and the passive thermal image, to obtain the absolute temperature value of the breast and cancerous tissue for any screening time period using the dual band property of the thermal camera, and to make comparison and determination of the ratio/difference of the active and passive thermal image (in single band and dual band imaging modes) obtained at different frequencies using the image and signal processing algorithms which are embedded in the control unit to detect the cancerous tissue (tumor tissue).

3. The medical electro-thermal imaging system of claim 2, wherein the current source is the multi-frequency voltage controlled alternating current source which injects controlled alternating currents in the frequency range of 0-1 MHz.

4. The medical electro-thermal imaging system of claim 2, wherein the control unit is configured to regulate the electric current that is provided by the current source to record image by the data provided by infrared camera and to make registration and comparison between the passive thermal image and active thermal image.

5. The medical electro-thermal imaging method of claim 1, wherein the analysis of the images is implemented by taking the electrical properties of tissue at operation frequency (electrical conductivity, electrical permittivity, and possibly magnetic permeability) into account.

6. The medical electro-thermal imaging method of claim 1, wherein the analysis of the images is made by collecting dual or multi-frequency data.

7. The medical electro-thermal imaging method of claim 1, wherein the positions and the number of electrodes are optimized so as to increase temperature and image contrast.

8. The medical electro-thermal imaging system of claim 2, wherein a dual-band (MWIR/LWIR) thermal camera in active mode of operation is used.

9. The medical electro-thermal imaging method of claim 1, wherein transient image analysis with more data is also implemented in addition to the steady-state imaging analysis.

* * * * *